United States Patent
Goldau (10) Patent No.: US 11,000,642 B2
(45) Date of Patent: May 11, 2021

(54) APPARATUS AND METHOD FOR GENERATING DIALYSATE FOR DIALYSIS

(71) Applicant: Fraunhofer-Gesellschaft zur Förderung der angewandten Forschung e.V., Munich (DE)

(72) Inventor: Rainer Goldau, Kastorf (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 263 days.

(21) Appl. No.: 16/316,510

(22) PCT Filed: Jul. 24, 2017

(86) PCT No.: PCT/EP2017/068642
§ 371 (c)(1),
(2) Date: Jan. 9, 2019

(87) PCT Pub. No.: WO2018/015571
PCT Pub. Date: Jan. 25, 2018

(65) Prior Publication Data
US 2019/0224401 A1    Jul. 25, 2019

(30) Foreign Application Priority Data
Jul. 22, 2016  (EP) ..................................... 16180923

(51) Int. Cl.
*A61M 1/36* (2006.01)
*A61M 1/28* (2006.01)
(Continued)

(52) U.S. Cl.
CPC .......... *A61M 1/369* (2013.01); *A61M 1/1656* (2013.01); *A61M 1/1696* (2013.01);
(Continued)

(58) Field of Classification Search
CPC .. A61M 1/1656; A61M 1/1696; A61M 1/287; A61M 1/369; A61M 2205/3606;
(Continued)

(56) References Cited

U.S. PATENT DOCUMENTS 3,878,564 A  4/1975 Yao et al.
4,572,785 A  2/1986 Braaten
(Continued)

FOREIGN PATENT DOCUMENTS

CN  1366466 A  8/2002
CN  1654108 A  8/2005
(Continued)

OTHER PUBLICATIONS

International Search Report, issued in International Application No. PCT/EP2017/068642, dated Oct. 11, 2017, pp. 1-3, European Patent Office, Rijswijk, Netherlands.
(Continued)

*Primary Examiner* — Dirk R Bass
(74) *Attorney, Agent, or Firm* — Brinks Gilson & Lione (57) ABSTRACT

An apparatus for generating dialysate for dialysis comprising a dialysate outlet and a dialysate inlet and dialysate purifying means, wherein the purifying means comprise a cryopurifier for generating pure water, wherein the inlet of the cryopurifier is connected to the dialysate outlet and the outlet of the cryopurifier is connected to the dialysate inlet; and a method for reclaiming of fresh dialysate from ultrafiltrate and wasted dialysate extracted from a dialysis patient, comprising the following steps: preparing an ice slurry from the dialysate, wherein the ice slurry contains ice crystals and a liquid containing solutes; and separating the ice crystals from the liquid containing the solutes.

20 Claims, 2 Drawing Sheets

(51) Int. Cl.
| | |
|---|---|
| A61M 1/16 | (2006.01) |
| B01D 9/00 | (2006.01) |
| B01D 9/04 | (2006.01) |
| C02F 1/22 | (2006.01) |
| C02F 103/02 | (2006.01) |

(52) U.S. Cl.
CPC .......... *A61M 1/287* (2013.01); *B01D 9/0004* (2013.01); *B01D 9/0013* (2013.01); *B01D 9/0036* (2013.01); *B01D 9/0063* (2013.01); *B01D 9/04* (2013.01); *C02F 1/22* (2013.01); *A61M 2205/3606* (2013.01); *A61M 2205/8268* (2013.01); *A61M 2205/8293* (2013.01); *A61M 2209/088* (2013.01); *B01D 2009/0086* (2013.01); *C02F 2103/026* (2013.01)

(58) Field of Classification Search
CPC .. A61M 2205/8268; A61M 2205/8293; A61M 2209/088; B01D 2009/0086; B01D 9/0004; B01D 9/0013; B01D 9/0036; B01D 9/0063; B01D 9/04; C02F 1/22; C02F 2103/026
See application file for complete search history.

(56) References Cited

U.S. PATENT DOCUMENTS

| | | |
|---|---|---|
| 4,581,141 A | 4/1986 | Ash |
| 4,830,645 A | 5/1989 | Ghodsizadeh et al. |
| 5,944,684 A | 8/1999 | Roberts et al. |
| 2003/0097086 A1 | 5/2003 | Gura |
| 2003/0187380 A1 | 10/2003 | Botto et al. |
| 2005/0274658 A1 | 12/2005 | Rosenbaum et al. |
| 2009/0120864 A1 | 5/2009 | Fulkerson et al. |
| 2010/0100027 A1 | 4/2010 | Schilthuizen et al. |
| 2014/0061127 A1 | 3/2014 | Cabrera et al. |
| 2015/0093812 A1 | 4/2015 | Ott |

FOREIGN PATENT DOCUMENTS

| | | |
|---|---|---|
| CN | 101048217 A | 10/2007 |
| CN | 201458848 U | 5/2010 |
| CN | 104491941 A | 4/2015 |
| CN | 104826185 | 8/2015 |
| CN | 105142692 A | 12/2015 |
| CN | 105658293 A | 6/2016 |
| DE | 7315909 U | 10/1973 |
| DE | 30 10 414 A1 | 9/1981 |
| DE | 4302319 A1 | 11/1993 |
| EP | 2 087 916 A1 | 8/2009 |
| EP | 2 277 572 A1 | 1/2011 |
| EP | 2 281 591 A1 | 2/2011 |
| EP | 2 277 572 B1 | 2/2012 |
| EP | 2 862 584 A1 | 4/2015 |
| EP | 2 446 908 B1 | 7/2015 |
| GB | 2 124 511 A | 2/1984 |
| JP | 06-134448 A | 5/1994 |
| JP | H11-137672 A | 5/1999 |
| JP | A 2005-509496 | 4/2005 |
| WO | WO 95/02559 | 1/1995 |
| WO | WO 2009/083011 A2 | 7/2009 |
| WO | WO 2011/031610 A1 | 3/2011 |
| WO | WO 2013/025844 A2 | 2/2013 |
| WO | WO 2013/052680 A2 | 4/2013 |
| WO | WO 2014/128293 A1 | 8/2014 |

OTHER PUBLICATIONS

European Search Report, issued in European Application No. 16180923, dated Jan. 19, 2017, pp. 1-2, European Patent Office, Munich, Germany.
W. F. Kuhs et al., "The Structure of Ice Ih by Neutron Diffraction," The Journal of Physical Chemistry, DOI: 10.1021/j100244a063, dated Oct. 1983, pp. 4312-4313, vol. 87, No. 21, published by American Chemical Society, Washington, D.C.
Anonymous, "Supercooling," dated Nov. 3, 2018, pp. 1-5, published online by Wikipedia at URL https://en.wikipedia.org/w/index.php?title=Supercooling&oldid=867128421.
Michael J. Blumenkrantz et al., "Applications of the Redy® Sorbent System to Hemodialysis and Peritoneal Dialysis," Artificial Organs, dated Aug. 1979, pp. 230-236, vol. 3, No. 3, published by Wiley, Hoboken, NJ.
Flore Duranton et al., "Normal and Pathologic Concentrations of Uremic Toxins," Journal of the American Society of Nephrology, 1258-1270, dated Jul. 1, 2012, pp. 1-13, vol. 23, Issue 7, published by The American Society of Nephrology, Washington, D.C.
Anonymous, "The European Uremic Toxin (EUTox) Work Group of the ESAO and endorsed Work Group of the ERA-EDTA," Retrieved from the Internet on Jul. 20, 2016, pp. 1, published by European Society for Artificial Organs at URL https://www.uremic-toxins.org.
Claudio Ronco, "Wearable Artificial Kidney: State of the Art," dated 2015, pp. 1-115, published by International Renal Research Institute, Vicenza, Italy.
John M. Walker et al., "Evaluation and Selection of Activated Carbon for Hemoperfusion," Kidney International, dated 1976, pp. S-320-S-327, vol. 10, published by The International Society of Nephrology, Brussels, Belgium.
Lise Bankir, "Active Urea Transport in Lower Vertebrates and Mammals," Urea Transporters, Subcellular Biochemistry, ISBN 9789401793421, dated 2014, pp. 193-226, vol. 73, published by Springer Science + Business Media Dordrecht, Springer Netherlands, New York City, New York.
Hiroaki Ozaki et al., "Rejection of Organic Compounds by Ultra-Low Pressure Reverse Osmosis Membrane," Water Research, dated 2002, pp. 123-130, vol. 36, published by Elsevier Science Ltd., Amsterdam, Netherlands.
Richard M. Lueptow et al., "Rotating Reverse Osmosis for Wastewater Reuse," dated Sep. 2004, pp. 555-586, published online by ResearchGate at URL https://www.researchgate.net/publication/24391817_Rotating_Reverse_Osmosis_for_Wastewater_Reuse?enrichId=rgreq-93b8539b6e0ed6b05d3719f034d815b3-XXX&enrichSource=Y292ZXJQYWdIOzI0MzkxODE3O0FTOjlwMzYyMDcwOTYwNTM5MEAxNDI1NTU4MzY4ODg2&el=1_x_2&_esc=publicationCoverPdf.
Jonathan Himmelfarb et al., "Measurement and Estimation of Kidney Function," Chronic Kidney Disease, Dialysis, and Transplantation, Third Edition, ISBN 9781437737714, Chapter 2, dated Oct. 22, 2010, pp. 35, published by Elsevier Saunders, Philadelphia, Pennsylvania.
William Drukker et al., "Dialysate Regeneration," Replacement of Renal Function by Dialysis, Third Edition, dated 1989, pp. 417-438, published by Kluwer Academic Publishers, Dordrecht, Netherlands.
Martin Chaplin, "Hexagonal Ice (Ice Ih)," Water Structure and Science, dated Mar. 3, 2016, pp. 1-5, published by Martin Chaplin at URL file:///K:/Clients/15991%20-%20Fraunhofer%20(Friese%20Goeden)/051%2031007/%20PWOUS/IDS/LiteraturCrypPurification_PatentRainerGoldau/MartinChaplin_HexagonalIce/Hexagonal%20ice%20ice%20Ih.htm.
Martin Fitzner et al., "The Many Faces of Heterogeneous Ice Nucleation: Interplay Between Surface Morphology and Hydrophobicity," Journal of the American Chemical Society, dated Oct. 4, 2015, pp. A-L (1-12), vol. 137, No. 42, published by American Chemical Society, Washington, D.C.
Marjatta Louhi-Kultanen, "Concentration and Purification by Cristallization," Acta Polytechnica Scandinavica, Chemical Technology Series, No. 241, ISBN 1239-0518, dated 1996, pp. 1-112, published by the Finnish Academy of Technology, Helsinki, Finland.
C.J. Van Oss, "Surface Tension Parameters of Ice Obtained from Contact Angle Data and From Positive and Negative Particle Adhesion to Advancing Freezing Fronts," Journal of Adhesion Science and Technology, dated 1992, pp. 503-516, vol. 6, No. 4, published by Taylor & Francis, Abingdon, VA.
Christoph C. Pradzynski et al., "A Fully Size-Resolved Perspective on the Crystallization of Water Clusters," Science, ISSN 0036-8075, (56) References Cited

OTHER PUBLICATIONS dated Sep. 21, 2012, pp. 1529-1532, vol. 337, published by the American Association for the Advancement of Science, Washington, D.C.

A. K. Lyashchenko et al., "X-Ray Investigation of Ammonium Fluoride—Ice Systems," translated from Zhurnal Strukturnoi Khimii, dated Jul. 1969, pp. 724-725 (616-617), vol. 10, No. 4, published by N.S. Kurnakov Institute of General and Inorganic Chemistry, Academy of Sciences of the USSR, Moscow, Russia.

R. Brill et al., "Mixed Crystals of Ice and Ammonium Fluoride," Nature, dated Feb. 13, 1954, pp. 316-317, vol. 173, No. 4398, published by Nature Publishing Group, London, UK.

Anonymous, "Ammonium Fluoride," dated Oct. 30, 2017, pp. 1-3, published online by Wikipedia at URL https://en.wikipedia.org/w/index.php?title=Ammonium_fluoride&oldid=807867958.

G. Durand et al., "Effect of Impurities on Grain Growth in Cold Ice Sheets," Journal of Geophysical Research, dated 2006, pp. 1-18, vol. 111, F01015, published by the American Geophysical Union, Washington, D.C.

Atsuko Kobayashi et al., "A Method for Making Large Agglomerated Ice Crystals for Freeze Concentration," Journal of Food Engineering, dated 1996, pp. 1-15, vol. 27, published by Elsevier Science Limited, Great Britain.

Chinese Office Action with English language translation for Chinese Patent Application No. 201780038880.3, dated Jan. 21, 2021, 14 pgs.

Japanese Office Action with English language translation for Japanese Patent Application No. 2018-561593, dated Mar. 8, 2021, 6 pgs.

APPARATUS AND METHOD FOR GENERATING DIALYSATE FOR DIALYSIS

CROSS-REFERENCE TO RELATED APPLICATIONS

This application is a 371 nationalization of international patent application PCT/EP2017/068642 filed Jul. 24, 2017, the entire contents of which are hereby incorporated by reference, which in turn claims priority under 35 USC § 119 to European patent application 16180923.1 filed on Jul. 22, 2016.

TECHNICAL FIELD

The invention relates to an apparatus and a method for generating dialysate for dialysis.

DETAILED DESCRIPTION

The prior art apparatus and methods for generating dialysate for dialysis are facing the following problems:

a) Availability of Pure Water

Availability of pure water is not omnipresent: Dialysate—the rinse fluid in close contact to the patients blood during dialysis—has to fulfill extremely high purity specifications. Complete absence of endotoxins, bacteria fragments and uremic toxins is essential to non-hazardous dialysis. Further specific concentrations of different types of ions, bicarbonate and glucose has to be matched prior to first contact to the blood.

A standard hemodialysis regime comprises 3 sessions per week, each 4 h of duration with a continuous dialysate flow of at least 300 ml/min. Therefore one week of dialysis of one patient requires approximately 220 l of ultrapure dialysate. The preparation of this amount is straightforward in countries where potable water and electricity is sufficiently available to operate reverse osmosis units from good quality tap water.

It is an insurmountable obstacle however in countries that are lacking these resources. Even the survival of patients who require dialysis is at risk under these circumstances.

It would be a great advantage if no pure water from external resources was needed for dialysis. The same applies to wearable units having no access to external water resources.

b) Removal of Uremic Toxins

Uremic toxins are manifold—as the methods adopted to clear them within one system:

Activated char coal is used for adsorption of a diversity of molecule types immobilized urease is adopted to catalyze the urea—ammonia reaction with NH3 product as charcoal adsorption is low for urea and reverse osmosis cannot separate urea sufficiently alone.

alternatively ammonium carbonate is generated and subsequently absorbed by Zirconium phosphate (REDY® System)

hydrated Zirconium oxide and carbon removes urea residuals, but does not remove the other uremic toxins.

reverse osmosis filters remove further particles and ions if operated properly.

many of the uremic toxins and retention solutes are still unknown or subject of open discussions.

98 of 130 solutes have been listed as uremic toxins later than 2007 (as of March 2016); 68 of them free water solutes—the process is still going on and it is uncertain what uremic toxins will be identified in future.

some of the smaller solutes cannot be separated by filtering or atmospheric pressure distillation as they are transferred as aerosols or boil below 100° C. (e.g. dimethylamine and other amines, urea).

some of them experience decomposition by heat (e.g. guanidine, proteins/middle-molecules), which cannot be controlled, because the size of compounds and type of removability (filtering, absorbing . . . ) is unspecified.

blood concentration limits for uremic toxins with respect to healthy individuals are still subject of scientific discussion. Therefore the skilled person does not have a valid specification of the reduction ratio to be accomplished. Accordingly it is difficult to choose an appropriate method.

some constituents are deposited in quantities that are not compatible to a reverse osmosis filters function (urea and layer forming proteins).

at high urea concentrations urea based chaotropic protein denaturation generates undefined protein decomposition successors. In technical terms there is a high variability of different substances with different approaches of removal. In particular reverse osmosis filters are prone to obstruction by these substances if their pores are of size below 1 nm that permits urea removal.

The more substances of unknown properties are to be extracted by a given process the more the technical approach of extraction will be a compromise.

efficient reverse or forward osmosis needs high pressures.

c.) Power Supply

In the vast majority of those countries where access to pure water is an issue also access to capable ac power supply is compromised. Electrical power is the most versatile form of energy which allows a high degree of technical freedom realizing different approaches to remove the uremic toxins. Driving pumps may be possible from accumulators, driving reverse osmosis units using high pressure will need mains access, driving distillation will need even more electrical power which has to be cooled and therefore is essentially lost. It would be advantageous if the dialysate purification device could be run on low energy requirements. It would also be advantageous if the system was designed to have low power consumption that can be sourced from photovoltaic solar panels.

d) Non-Stationary Operation

Decentralized operation and in a second step wearability needs more than only independence from supply mains.

There are some essential and combined requirements that are advantageous to be fulfilled in order to allow decentralized (home dialysis) operation, overnight operation and even further to maintain wearability of an artificial kidney:

The gross weight should be less than 6-8 kg (in a first approach, further reduction is advantageous).

Outer shape should be designable such that it can be integrated into waist belts, backpacks or vests or at least is in a size able to be transported in small vehicles.

Sufficient and equivalent clearance for all known and unknown uremic toxins, high dialysate purity.

Independent of external power and water supply.

Sufficiently silent to be worn or placed in meetings or quiet environments.

No interference with orientation in gravity field (This might be problematic if distillation is used.).

No disturbing or adverse exhaust, heat or malodor.

Independent, maintenance free operation during reasonable periods like 4-8 h.

High safety requirements and safe shutdown or alarm in adverse situations, operation possible without regular daily medical supervision.

Option of data logging and network connection to the hospital desirable to identify and remedy critical situations externally.

Off facility simple and quick maintenance by the patient himself/herself without daily technical support and logistics.

No replacement of disposables like sorbents, cartridges or substrates needed for filtering which cannot be accomplished by the patient himself/herself or which is not available at low cost and acceptable logistics.

A reliable and sanitary vascular access that can be handled by the patient alone during all day dialysis.

No cooling chains for catalytic agents.

Absence of aluminum in absorbent/ion exchanger/urease carrier due to its compromised role in long term mental outcome and bone health.

No additional sodium or pH buffer load by cations released in exchange to ammonium ions from ion exchanger/urease.

Phyisiological dialysis would be a mandatory long term objective, e.g. controlling sodium, glucose and ultrafiltration according to internal body parameters, e.g. blood sodium or blood volume. A long term uncontrolled dialysis will have to closely follow the patients constitution and fluid state which may vary largely within the periods of new prescriptions by a physician.

Finally the costs must be considerable low in particular in developing countries.

At the time being it might be acceptable that a few of these requirements are solved. They can only be an indication to not misdirect endeavor and focus on today's most important issues—which are still pure water generation, independence of power supply, high security of the device, and reliable blood access which together allow unsupported low cost home dialysis to the indigent at all—wearability in this sense permits longer daily dialysis and therefore supports long term survival and outcome but is not essential to primary survival of those who have no access to dialysis at all.

Prior Art Solutions a) Non-Availability of Water

Different approaches do exist. They all comprise the purification of ultrafiltrate from the patient within a feedback loop. Most prior art inventions comprise a closed loop circuit that conducts the ultrafiltrate drawn from the patient blood within a more or less regular dialyzer to different kinds of units to purify them and afterwards returns it to the dialysate inlet. The water itself originates from the blood and stays within the liquid phase during the whole closed loop. Different approaches are used, even in combinations that cannot clearly be distinguished:

1. Simple Absorption of Ultrafiltrate Solutes or Ion Exchange and Subsequent Feedback (GB2124511, DE7315909, US2005274658).

These prior art documents comprise drawing ultrafiltrate from a dialyzer, conducting it on an adsorption unit or on a filter unit and feed it back to the dialysate. These solutions do not take into account the inability of charcoal absorbers to adequately bind urea or the high pressures needed for hyperfiltration or reverse osmosis. Nevertheless they can be regarded as one of the early approaches to regenerate self drawn dialysate and realize wearable artificial kidneys. The circuit of hemodialyzer, ultrafiltrate regeneration and feedback is already disclosed.

2. Electrosorption (EP 2 087 916 A1)

Materials with special affinity to uremic toxins are used as electrodes. Special materials with nanostructure, porosity or catalytic properties are used that bind uremic toxins. These methods have limited capacity and do not suit the need for high mass extraction.

3. Nanofiltration, Microfiltration Combined with Absorption or Reverse Osmosis (EP2277572B1, EP 2 281 591 A1)

The dialysate is filtered by a nanofiltration unit (e.g. special materials or reverse osmosis) and subsequently routed upon an adhesive material to absorb those substances that still passed the nanofiltration.

4. electrocatalytic decomposition and Electrosorption (EP 2 446 908 B1, EP 2 862 584 A1), in Particular of Urea.

This approach comprises the decomposition and degassing of uremic toxins solved in the dialysate. Electrodes with catalytic or activated surfaces are used and supplied with specific electric current. Also electronic means are taken to avoid electrode degeneration. The materials are mostly from the group of nanostructured sorption material, polymeric matrices or specific metals like Pt, Ni, Ti, Ir, Sn, Ta or Ru, oxides, oxyhydroxides and hydroxides and are shaped plane, circular, tubular or like filaments/threads. In particular urea can be decomposed by electrolysis at a much lower voltage than needed for water electrolysis. Also cartridges are suggested to ease handling. This principle does not work for all solutes and cartridge logistics and costs are not acceptable for wearable home dialysis.

5. Graft on Demand by Bioartificial Tissue Engineering (Partially Quoted from US 2015/0093812 A1)

A decellularized seeding system is used to seed glomeruli-type structures on a filtration organ scaffold (lung or other organs like kidney), which are cultivated under controlled pressure environment. Even afferent and efferent vessels are generated by this technique. After a seeding phase the initial kidney constructs can be transferred to a perfusion bioreactor to provide whole organ culture conditions and bring the tissue to the next step of maturity. Finally it can be used for filtration—described here very briefly. This approach seems to be very promising in the long run but today is still far from being applicable to humans.

6. Electrochemical Detoxification (U.S. Pat. No. 3,878,564)

Using electrolysis most of the solvents are regarded to be oxidizable by radicals generated by electrolysis or are converted into harmless products like water, $CO_2$ and nitrogene. Some of the files lack of detailed chemical reaction disclosure, but for urea it works and can avoid sorbents. Also an electrochemical ammonia reactor is comprised. Substances listed here comprise NH, NH+, urea, uric acid, digitalis glycosides, carbon monoxide, barbiturates, ketone bodies, aceto acetate, methanol, creatinine, alanine, ethanol, and mixtures thereof. The drawback is that radicals and chlorine oxidants may occur, any of them must be safely reduced by additional charcoal layers before the water may have blood contact again. There is a certain hazard risk.

7. Urease Based Decomposition and Ion Exchange Layer in Sorbents (e.g. U.S. Pat. No. 4,581,141, similar Redy® System and Later Derivates Like Allient® or Dialysorb®)

This is the most promising approach. Urease is immobilized (sometimes on an aluminum containing carrier) to act on urea which decomposes to bicarbonate and ammonium. The system is integrated into one of the known hemodialysis methods. The basic principle after urea decomposition is ion exchange and catalytic conversion. The large amount of ammonium to be exchanged before dialysate may have contact to blood enforces high amounts of ion exchange mass. The protons generated from urea by urease tend to decrease pH and therefore are a load to the bicarbonate buffer. The system therefore is discussed to be suitable for bicarbonate dialysis.

There is a risk of a filter break through when overloaded with ammonium which is hardly to detect by sensors. Further the ions exchanged may adversely influence the body's electrolyte balance and pH buffering. Aluminum carriers have been discussed to be very critical.

This principle does not cover all substances but addresses one of the most prominent waste dialysate constituents—urea—properly and has undergone essential development and a certain acceptance but is still not widespread accepted due to costs, logistics, some long term outcome concerns and the filter breakthrough/overfeeding apprehension mentioned.

8. Combination of Ion Separation with Electrodialysis and Enzymatic Urea Decomposition (DE 3010414 A1)

Electrodialysis is a principle which comprises several chambers, each with two electrodes of different polarity. The chambers are separated by the electrodes themselves and the electrodes are semipermeable for the ions they do not attract by their polarity. Therefore different chambers can be located contiguously and build a system of high throughput which is capable to reduce ions. Different types of membranes and carrier molecules are used to address specific ions. Not all of the substances can be addressed.

9. Other Combinations of the Above Mentioned Systems are Envisaged (WO95/02559)

In this prior art document an electrolysis cell is used to generate hypochlorite. The fluid is then conducted to a degassing unit, a charcoal filter unit and a zeolite filter unit using urease. The detailed reasons for the combination have not been disclosed.

10. Electrophoresis Blood Purification (US2003187380A1)

An electric field is applied to remove metabolic components from plasma or blood using membrane based electrophoresis. Applied voltages are up to 200V and even hemolysis is discussed (0.05% of red blood cells lysed after single pass). Many different types of substances can be addressed, but the mechanism of specificity is not laid open within this prior art document.

11. An Approach to Clear Urine Using Distillation of Water has Only been Found for Spacecraft Systems (US20140061127).

Distillation is a principle that addresses the water and low boiling solutes but can only work in continuous flow if no low-boiling solutes are existing. Further urea cannot be distilled completely. Many of the amines found in urine are low boiling and therefore distilling alone does not cover all requirements. Further gravity aspects need to be taken into account. Distilling water in all positions may impose some technical issues and requires high energy consumption. Also a bioreactor to contact urea to immobilized urease (granulated activated carbon-urease) is mentioned in this prior art document, with the generated ammonia conducted to a subsequent electrochemical cell to provide electrical energy. Finally molecular nitrogen and water is produced. This system aims to not loose any of the substances.

Forward osmosis that in a first step extracts water from the system by osmolarity is the only principle aside distilling that address the solvent and not the solutes. This is advantageous, but if osmotic forces are used high osmolarity is needed. Although the engineers are free to use ions that suit the needs a further reverse osmosis step is needed to extract the water again from the high osmotic solution. It reduces the number of different solutes offered to reverse osmosis but is water consuming. Further it cannot separate urea that comes with the solvent drag.

Also UV irradiation has been suggested, which does not extract solvents and therefore is not a convenient solution for generation of ultrapure dialysate.

The above listing of the different solutions to purify dialysate from uremic toxins demonstrates that there are very specific solutions to specific solutes and a manifoldness of different approaches.

The solutions to clear the ultrafiltrate are diverse and use many different techniques including effects of an electric field on the solutes, adsorbing the solutes, subject them to chemical reactions mainly of catalytic type or immobilizing them on specific membranes. Many approaches need disposables and supply chains therefore. A technical system dealing with all relevant—and still unknown—substances will surely consist of combinations of the above mentioned methods. This makes the devices complicated.

Accordingly it is an object of the invention to provide an apparatus and a method for generating dialysate for dialysis which does not require pure water for purifying dialysate.

b) Uremic Toxins

In the prior art there is diversity of methods to remove uremic toxins from the dialysate. The above listing of the different solutions to clear dialysate from uremic toxins demonstrates that there are very specific solutions to specific solutes.

Adsorption, catalytic reactions and ultrafiltration/reverse/forward osmosis are used for urea and middle size molecules:

Urea may be regarded to be the lead substance of uremia—as the name indicates—thus urea is a main constituent of the human urine. Urea cannot be adsorbed in high amounts by charcoal without refrigeration. 200 g of active charcoal are capable to absorb 2-3 mg of urea. Urea excretion is estimated to be 5.7 mmol/d/kg of bodyweight. This is for a 75 kg person 430 mmol/d or 25 g/d, strongly depending on the diet. This amount cannot be absorbed by charcoal in reasonable quantities. Therefore reverse osmosis (RO) is considered to remedy the situation. RO is not the favourite method to remove urea, as urea molecule radius is in the range of 0.18 nm. This is quite similar to water (which has a diameter of 0.31 nm or a bit less calculated from molar volume). Therefore urea as an undissociated molecule, which experiences no charge repelling forces, can hardly be extracted just by pore size and/or a molecular sieve.

Further pore sizes and/or a molecular sieves are even a bit larger by technical reasons, as the overall fluid must be sufficient and the pressures must not exceed the membrane stability.

The effective membrane pores (there are not really pores, it is just a model) show calculatory equivalent sizes of 0.33 nm to 0.44 nm. Typical rejection rates are as low 0.2-0.3 therefore.

This means 70-80% of urea are still found in filtrate after single pass RO. Several equivalent passes (recirculations) with additional pump energy input are needed. Further the filter water is also split per RO pass. Typically only 50% pass the membrane. If 70% of urea pass the membrane, but only 50-60% of the water, urea is enriched in the filtrate—contrary to all the other solutes that are retained. This is due to the water ability to build hydration shells. This makes RO infeasible if applied simultaneously for non urea solutes.

Most ultra low pressure membranes are multi-layer thin film composites of polymers. The transport process therefore has diffusive character obeying Stoke's equation and is prone to obstruction by the load. The retention rates for urea are typically measured at 0.17 mmol/l. Typical plasma urea concentrations which would roughly appear in dialysate would be 5 mmol/l, which is 30 times higher. It is unclear whether filters will work sufficiently for prolonged periods at higher concentrations. Even NASA related scientists Cabrera et al. are led "to the conclusion that urea is still hard to reject by such membranes" (US20140061127).

Further high effort is taken to make RO units work reliable and enduring. Substance layers stemming from filtration solutes are obstructing the membranes and its interior reducing effectivity or increasing fouling. In particular rotational movement of the membrane (which is additional mechanical effort) seems to have counter-fouling effect and is discussed for spacecraft water reclamation.

If the reverse osmosis system is used in the immediate vicinity of the patients there is a further serious drawback:

Any reverse osmosis system needs pumps that generate pressures in the range of 500 kPa-4000 kPa or even more and therefore will not work completely silent. It is a challenge of mechanical construction to make them operate at sufficiently low noise in quiet environments as necessary if a patient uses the device in his/her daily life.

Urea decomposition by enzymes (urease) is a method to make urea fragments accessible to further treatment like ammonium electrolysis cells or separation. NH3 is a high energy molecule which can be metabolized to molecular nitrogen and water.

Other small and middle-molecule solutes can more easily be filtered by size exclusion even if the rejection rates are far below and not optimal. Reverse osmosis filters are established to clear any substances of significantly higher molecular radius than water as long as the load is not too high in absolute mass. RO systems will cover all specifications related to purity here—they will not cover the specifications with respect to water savings—as the retentate is lost—and to noiselessness. Energy supply for the pump must be electrical and is in the range of 10 W per l/h.

Methods like adhesion, adsorption, reverse and forward osmosis, catalysis or other chemical reactions and distillation are quiet elaborated meanwhile but may still suffer from inconvenient practicability, durability, reliability, specificity and functionality for a patient near or patient-worn system. It is not easy to build a technical system that fulfils the demands for removal of many different substances, part of them unknown. It would be advantageous to concentrate on only a few or only one substance. Further the costs of applying these methods (e.g. sorbent cartridges) are too high for those living in countries where water is scarce.

Accordingly it is another object of the invention to provide an apparatus and a method for generating dialysate for dialysis which is essentially independent from the uremic toxins in the dialysate coming up in the future.

c.) Power Supply Issues

Any of the prior art dialysis systems need their energy in electrical form, most of them using AC. In particular wearable artificial kidneys discharge accumulators when being worn and need at least temporary mains supply to recharge them—which might be acceptable during periods of the patient being at rest. The drawback is that there are many countries with enormous numbers of end stage renal disease (ESRD) patients that cannot maintain a stable and powerful decentralized electrical network, besides the water lacking. Even for hospitals this can be a challenge, in particular in crisis situations—dialysis cannot be interrupted for weeks during hospital recovery after war impact. A conventional hemodialysis device will need at least 1000 W of reliable, uninterrupted AC electrical power during certain periods of rinsing, cleaning or heating and a few hundred W during regular treatment. It would be desirable to perform dialysis independent from external mains as electrical power be supplied by solar panels in many of those countries lacking of reliable power network.

When developing a home dialysis device or even a wearable artificial kidney in a first approach, it should be acceptable to use electrical power temporarily even from cord. However a further development step should be the complete independence from high current electrical supply. A solar panel might be a reasonable compromise to operate dialysis.

Accordingly it is another object of the invention to provide an apparatus and a method for generating dialysate for dialysis which is energy efficient.

d) Decentralized Operation as an Artificial Kidney

The outstanding issue beside power supply is the lack of water availability. Water is not omnipresent in countries of equatorial latitudes, but solar power might be sufficient—in particular if there is a way to store energy in chemical form. All other shortcomings like logistics for maintenance, filters and other spare-parts like cartridges or lack of local technical and medical expertise in principle can be resolved even in less developed countries compared to the dialysis water deficiency, which is hard to overcome.

To solve this problem the prominent solution suggested in the prior art is the use of reclaimed dialysate or ultrafiltrate from the patient himself/herself within a feedback loop and reclaiming it using one or several of the methods mentioned above. This principle has been suggested in numerous prior art documents (US2003097086, EP2281591, US2010100027, WO09083011, WO11031610, DE7315909) and has already led to wearable artificial kidneys.

Probably not all requirements decentralized or wearable dialysis imposes could be fulfilled in a first approach as the past has shown. Although different and encouraging devices during the last 35 years have come up and demonstrated that wearable artificial kidneys are possible and can keep patients alive for periods measured in years, these systems have not found widespread acceptance up to now. Not only technical restrictions but also some concern about the treatment equivalence, toxicity and filter break through, related with drawbacks to electrolyte and acidity metabolism, home dialysis vascular access handling and long term outcome may be the reason, as well as the costs for adsorbent cartridges—which are hardly accepted for daily wearable dialysis. One may speculate if there are other reasons than technical inconvenience—but doubtlessly still technical aspects are not satisfying. Particular effort is necessary to address essential requirements like power-, water- and adsorbent-independence, uncompromised clearance equivalence, silence, handiness and in case of intended wearability low weight. Further a very silent internal power generation would be advantageous to at least keep the essential components like pumps, control logic and external connections operating if accumulator capacity is running short.

Systems that address the need of indigent patients that cannot pay for continuous medical supervision are further obliged to be very moderate in treatment costs and the treatment handling of such systems without continuous medical support must be simple, inherently safe and easy to handle. To imagine a trained patient performs dialysis by himself/herself for longer periods (several months) without medical supervision (as an alternative to death) implies a much more crucial clearance and blood parameter observation than in hospital dialysis. The system should further be able to clear and purify reuse filters with pure water. One of the remaining drawbacks of all existing technology that works with ultrafiltrate is that it can only act adequately on known solutes. Unknown solutes may or may not be effectively cleared from the dialysate and have potential to enforce technical modifications. Beside a non-total solute removal of the known uremic toxins this is the reason why it cannot be guaranteed that the treatment quality is equivalent to a regular pure water and reverse osmosis fed hemodialysis system. It is obvious that matching all requirements is still an enormous endeavor and it would also be a significant leap to address the majority of them successfully. The present invention is aimed to improve some of them, not all. In some aspects it goes a bit further than existing techniques.

Methods like distillation, adsorption or using high pressure pumps (reverse osmosis) do not fully match essential requirements like sufficient independence of electrical energy or water and disposable supply, handiness, treatment equivalence and costs. Toxicity from cartridge released substances and infections are further concerns. There are still unresolved issues with prior art methods.

Accordingly it is another object of the invention to provide an apparatus and a method for generating dialysate for dialysis which is independent from external water and energy supply.

According to the invention there is provided an apparatus for generating dialysate for dialysis comprising a dialysate outlet and a dialysate inlet and dialysate purifying means, wherein the purifying means comprise a cryopurifier for generating pure water, the inlet of the cryopurifier is connected to the dialysate outlet and the outlet of the cryopurifier is connected to the dialysate inlet.

According to the invention the cryopurifier can be similar as a freeze concentrator with the difference that the pure water is the product to be used and the concentrate is discharged. Accordingly any freeze concentrator known to the skilled person can be used which is suitable for the invention and can be adapted to the dialyzer.

According to the invention the cryopurifier can comprise an ice crystal growth container and a wash column.

According to the invention the outlet of the cryopurifier can be a pure water outlet being connected to the dialysate inlet.

According to the invention a cryopurifier can be combined with a standard dialysate means to provide an apparatus in accordance with the invention.

According to the invention dialysate prepurifying means can be provided between the dialysate outlet and the cryopurifier inlet.

According to the invention dialysate postpurifying means can be provided between the cryopurifier outlet and the dialysate inlet. This embodiment provides the advantage that the life-time of the postpurifying means, for instance a reverse osmosis purifying means can be increased. Furthermore it may be possible to provide for water to be used with other patients and/or for desinfection purposes of the apparatus and other medical devices.

According to the invention heat exchange means can be provided for providing heat exchange between the cryopurifier inlet and a heater at the cryopurifier outlet.

According to the invention heat exchange means can be provided for providing heat exchange between the cryopurifier inlet and a heater at the wash column outlet.

According to the invention the apparatus can be separated into a base station and a wearable unit.

According to the invention the apparatus can comprise a docking interface for connecting the base station with the wearable unit.

According to the invention the purifying means and/or the cryopurifier can be integrated in the wearable unit.

According to the invention the dialysate inlet can be the inlet of a hemodialysis machine and the dialysate outlet can be the outlet of the hemodialysis machine.

According to the invention the dialysate inlet can be the inlet of a dialyzer and the dialysate outlet can be the outlet of the dialyzer.

According to the invention the dialysate inlet can be a peritoneal dialyse inlet and the dialysate outlet can be a peritoneal dialyse outlet.

According to the invention there is also provided a method for reclaiming of fresh dialysate from ultrafiltrate and wasted dialysate extracted from a dialysis patient, comprising the following steps:

(a) preparing an ice slurry from the dialysate, wherein the ice slurry contains ice crystals and a liquid containing solutes; and (b) separating the ice crystals from the liquid containing the solutes.

According to the invention the amount of pure water to be refed to the dialyzer can and should be regulated such that the patient is neither dehydrating nor overhydrating.

According to the invention in step (a) the temperature can be between 0° C. and the eutectic temperature, which is lower than 0° C.

According to the invention in step (a) a crystal seed can be used.

According to the invention a crystal growth activator can be applied in step (a). According to the invention the crystal growth activator can be glucose.

According to the invention in step (a) supercooling can be applied.

According to the invention in step (a) ice crystallization can be controlled by infrared and/or Raman spectroscopy.

According to the invention separating the ice crystals from the liquid can be obtained by cryopurifying and/or freeze concentrating.

With other word, freeze concentration can be used for obtaining the pure water in the form of ice crystals at sub-zero temperatures. Preferably one crystallizer and one wash column can be used. The crystallizer can be a vessel with a cooling jacket. The inner wall of the vessel can be scraped. The outer wall can be cooled by a circulating refrigerant. Ice production and crystal growth can take place inside the crystallizer. By varying residence time ice crystals grow, creating an optimal crystal size distribution for efficient separation can be achieved. In the wash column, the concentrated liquid can be separated efficiently from the ice crystals. A compressed ice crystal bed can be washed with melted ice to remove all traces of concentrated liquid.

According to the invention the apparatus can comprise a plurality of docking interfaces for connecting a plurality of portable units with the base station.

According to the invention the docking interface can comprise interfaces for connecting reservoirs provided in the base station and the wearable unit.

According to the invention the components of the apparatus can be separated in stationary and portable components to enhance its wearability.

According to the invention the apparatus can be separated into a basis unit (or basis station) and one or more wearable units. In case of more wearable units these wearable units may be used simultaneously, if the basis unit has an appropriate size.

The wearable unit may comprise a small reservoir for fresh and used dialysate, a pump device for pumping blood and dialysate, a dialysis filtering unit to be operated in countercurrent, a dosage unit for adding additives to the fresh water to obtain fresh dialysate, a control unit, a small hydrogen reservoir and an accumulator to provide sufficient energy to operate the device for a few hours.

Alternatively or in addition a hydrogen fuel cell (for running the wearable unit for a few hours) and/or a small accumulator to be used for starting up the wearable unit when the fuel cell is not running may be provided. In addition the wearable unit may comprise an interface matching to the interface of the basis unit, such that dialysate can be discharged and water, electrolyte, additives, hydrogen and be refilled for running the wearable unit and its fuel cell. The components should be designed to meet the needs of a wearable device, i.e. the total weight including materials should not exceed 6 to 8 kg. The patient can choose a tradeoff between amount of water uptaken and dialysis operation time until recharge to meet her personal weight needs when carrying the wearable artificial kidney.

According to an embodiment of the invention the wearable unit may comprise a complete cryopurifier wherein the complete dialysate purification system can be included for purifying the dialysate by freeze concentrating the dialysate and taking the pure water from the freeze concentration as dialysate to be recirculated to the dialysate outlet.

Based on the considerations of the steady growing number of uremic toxins identified and the fact that water will always be adopted for dialysis it is helpful to separate water and not uremic toxins from a given amount of spent dialysate or ultrafiltrate. Water can be identified by its molecular properties as there is outer shape and molecular geometry, length and strength of hydrogen bonds to other water molecules, charge distribution and polarization, atomic components, molecular elasticity and tensibility, molecular energy levels, its electrochemical properties like proton exchange and some more.

Some of the properties mentioned above are important for constituting an ice crystal lattice when frozen. By far with the most substances water will build an eutectic system which has a lower freezing point than water alone. As ice crystals grow they reliably exclude other molecules that remain in the liquid phase. Reducing temperature more and more but still above the eutectic melting temperature the external liquid phase will approach the eutectic point concentration. This is well known to the expert and can be used for purification.

Some of the knowledge of the skilled person relating to ice formation can be found on the following website, wherein its content is incorporated into this disclosure of the present invention by reference: http://www1.lsbu.ac.uk/water/hexagonal_ice.html.

At temperatures below 0° C. under atmospheric pressure water crystallizes with multiples of a hexameric box to a hexagonal crystal called ice Ih. All water molecules within ice Ih experience identical molecular environments with a moderate packing efficiency of roughly ⅓—so there is much interstitial space in the grid. The c grid constant (distance of the basal planes) with 0.7356 nm (at 250K) slightly differs from the ideal hexagonal symmetry c of 0.7378 nm—due to the molecules tensibility and H—O hydrogen bonding strength. The a constant (lateral lattice spacing) is 0.45181 nm.

The grid distances are typical for ice at a given temperature (250K) and atmospheric pressure. A high resolution neutron diffraction study on the molecular geometry of ice Ih can be found in "The Structure of Ice Ih by Neutron Diffraction", Kuhs W F, Lehmann M S, J Phys Chem 1983, 87, 4312-4313.

A molecules suitability to be inserted in such an ice Ih lattice strongly depends on its size, atomic composition, bond lengths, the number, direction and strength of hydrogen bonds that can be established to other neighbours. From the above mentioned literature it can also be concluded that even characteristic proton transfer properties are relevant for the stability of ice Ih (Grotthuss-Mechanism). For a molecule to participate in the ice Ih formation these matches are essential but not sufficient. This means a molecule must fulfil these conditions at a high degree if the process of ice freezing once has started to be inserted into the lattice. But it does not enforce the process of ice formation to start at all. It is a well known fact that pure water can be undercooled without freezing up to down to −40° C.

There is another condition to be fulfilled: Looking at the simplified situation of a spherical ice crystal the Gibbs free energy (ΔG) is relevant to decide if a granule or sphere of ice will grow at all. ΔG describes the amount of energy needed when a molecule transits from fluid to the ice phase. As long as ΔG is positive the transition will not occur, negative ΔG permits the transit to the ice sphere as energy is released. And vice versa:

Whenever for a molecule of water within the crystal the free energy after passage of the surface to the liquid outside phase is lower than the free energy it had inside it will leave the crystal. This is the case in particular with very small spheres with high surface tension. They tend to shrink. Therefore ΔG can be written as:

$$(G1) \Delta G = 4\pi r^2 \sigma - \frac{4\pi r^3}{3V_{mol}} RT\ln(1+S)$$

with r being the sphere's radius, σ the surface tension, S being the supersaturation ratio of the water near the interface according to the liquidus line in the eutectic phase diagram and temperature, R the gas constant, T the temperature and $V_{mol}$ the volume of a mole of water. The critical size $r_{crit}$ when the crystal will neither grow nor shrink—the minimum size for granulation—is defined by $$(G2) \frac{d\Delta G}{dr} = 0 = 8\Pi r\sigma - 4\Pi \frac{r^2}{V_{mol}} RT\ln(1+S)$$

$$r_{crit} = \frac{2\sigma V_{mol}}{RT\ln(1+S)}$$

G2 is known as the Gibbs-Thomson equation. Assuming nearly equilibrium conditions the supersaturation ratio S=concentration/equilibrium concentration should be near 1, immediately after granulation onset it will be slightly higher so an uncertainty remains in the following consideration.

Further σ strongly depends on the partner substances at the interface, the size of the sphere and the temperature. In particular for small spheres 6 grows. Values for σ can be obtained from the literature for flat surfaces. To get a very rough estimate of the lower limit of $r_{crit}$ we assume the apolar (Lifshitz-vdWaals-) surface tension of ice towards non-water molecules to be approximately 30 mN/m at 273.15 K, although real surfaces are not flat. Using this value one yields for raft 0.68 nm. A sphere of this size consist of about 50 water molecules. As long as the sphere is smaller it will not grow and therefore feed bigger ones in the neighbourhood (Ostwald ripening) at the cost of its own substance. As this is the lower limit it can be expected that ice crystals will only grow if they are significantly larger.

Non-water molecule agglomerations of that size may serve as crystallization seed if certain surface conditions further are fulfilled. Although the seeding process is much more complicated and still subject of scientific discussion it is a very rough estimate how large at least a seed must be. This is in coarse coincidence with the experimental results—the icosahedral clusters of liquid water typically contain 280 water molecules at a diameter of 3 nm. In their inner core the crystallization is reported to start with 275+/−25 molecules. The growing ice is supposed to exclude nearly all solutes at ambient pressure. There is only one exception from this rule where the molecular properties are very similar to water: ammonium fluoride. NH4F can be contained up to 7.4 mol % due to their structural similarity and is regarded to be the only substance that can build a solid solution with ice. Even the force of the restraining force that keeps particles and impurities outside the ice or moves the ice granulation—called the pinning effect—can be found in the literature:

$$(G3) F_{restrain} = n\sigma r_{particle}$$

which is in the range of 65 pN for the particle of $r_{crit}$. As such a particle has gravity forces of $10^{-23}$N the very small impurities are lightweight enough that they can just be excluded by surface tension forces of the growing crystal. As $F_{restrain}$ grows by power of 1 with r, the gravity force by power of 3, the principle will work reliably only for impurities smaller than approximately 5 μm—a size that easily can be filtered even at high flow rates.

As long as ammonium fluoride is absolutely unexpected from the environment or from the patient it is safe to clear ultrafiltrate or dialysate using cryopurification.

Figure 1:
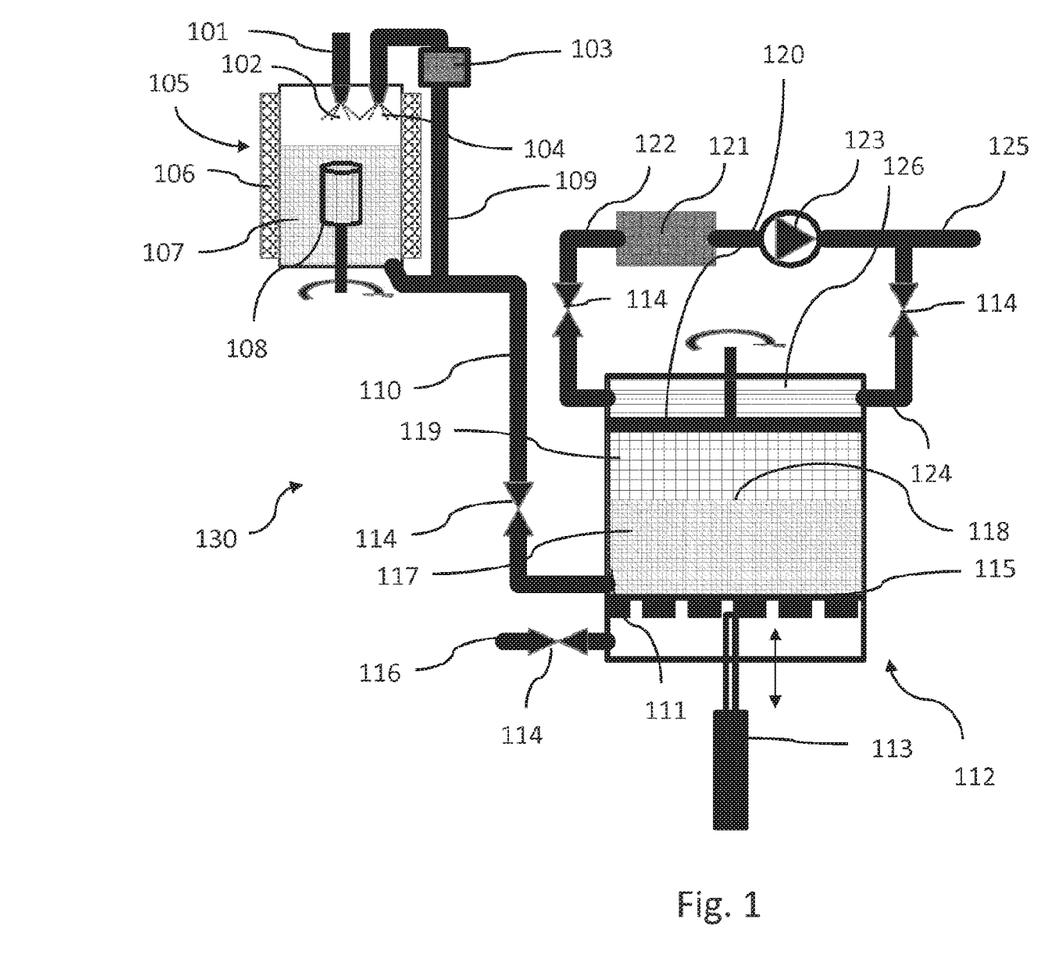
FIG. 1 is a schematic diagram of a first embodiment of the invention.

This principle of purifying water or other solvents that build crystals from contaminants is well known throughout the food and drinking industry and has experienced widespread use in large production plants. Surprisingly it can be adapted to dialysis, for instance with a setup depicted in FIG. 1 showing an exemplary cryopreparation of dialysate.

According to the invention the liquid containing the solutes can be analyzed like urine.

Urine is normally not available from patients being subject to dialysis. These patients do not have their own natural diuresis because of theft terminal renal insufficiency. However, the liquid containing the solutes obtained by the method and/or apparatus in accordance with the invention can be used as a kind of artificial urine because it will be concentrated sufficiently to be above the detection limits of the laboratory equipment, i.e. the dialysate will be purified and the liquid containing the solutes will be concentrated. This concentrate, i.e. the liquid containing the solutes, is not identical to natural urine because the method is optimized for the purpose of carrying out the dialysis. Nevertheless, it may be possible to derive clinical parameters from the artificial urine (the liquid containing the solutes) obtained in accordance with the invention similar as clinical parameters are derivable from real urine. Standard analytics may be performed, for instance regarding metabolic diseases (diabetes, hepatic dysfunction, etc.), because concentrations of the solutes can be reached which are sufficient for the equipment used for the analysis of natural urine. For calibration purposes the ratios of the concentrations of the various solutes can be used instead of the absolute concentration values because all components are concentrated by the same factor. The analysis of the artificial urine can also be used to optimize the equipment and parameters to be used for performing the method in accordance with the invention. Monitoring the concentration of the solutes will provide information about the efficiency of the method. Thereby appropriate filter types and clearance parameters can be defined to get acceptable and/or better results. The quality and/or purity of the dialysate can be improved thereby. This is advantageous with respect to known dialysis where the concentration of solutes cannot be determined because the concentration is below the detection limit of the laboratory equipment normally used.

The invention is described with reference to the figures showing embodiments of the invention, wherein the following reference signs will be used:

1 blood inlet
2 blood outlet
3 blood pump
4 dialyzer
5 ultrafiltrate transfer
6 dialysate inlet
7 dialysate outlet
8 SN or DN catheter
9 volume balancing unit
10 priming shunt
11 priming pump
12 ultrafiltrate dosage pump
13 spent dialysate reservoir
14 electrolysis unit
15 split gas exhaust means
16 garbage residuals line
17 heating means
18 hydrogen separation/pore size filter and/or molecular sieve
19 hydrogen pump
20 hydrogen reservoir
21 hydrogen fuel cell
22 pure water reservoir
23 photovoltaic solar panels
24 power and control unit
25 store means, e.g. NaCl, Bic, Anticoag
26 electrical power supply line
27 wearable hydrogen reservoir
28 hydrogen fuelk cell for power supply
29 pure water reservoir
30 fresh dialysate pump
31 local storage means, e.g. NaCl, Bic, Anticoag
32 dosage/admixture unit
33 power and control unit
34 docking interface
35 line for water from other sources (optional)
36 line for hydrogen from filter 18
37 oxygen from environment air
38 air
39 line for removing O2, NH3, Cl2

40 oxygen from environment air
41 dosage line
42 vein
43 dialysate reservoir
44 base station
45 wearable unit
101 dialysate inlet
102 dialysate inlet nozzle
103 Crystallizer-heater-cooler unit
104 Seed crystal inlet nozzle
105 Container for ice crystal growth
106 cooling jacket of 5
107 ice slurry
108 stirrer
109 feedback for seed preparation
110 slurry feed for wash column
111 slurry inlet to wash column
112 wash column (wc)
113 piston to push slurry through wc 12
114 valves for flow control
115 liquid phase filter
116 concentrate outlet
117 Mixture of liquid and solid phase
118 wash front
119 pure ice and pure liquid
120 rotating ice scraper
121 heater
122 pure slurry (solid and liquid) pipe
123 pump
124 pure water (liquid) feedback loop
125 pure water outlet for dialysis
126 pure slurry (solid and liquid)
130 cryopurifier
218 optional distiller and/or RO system in dialysate feed
236 optional heat exchanger FIG. 1 is a schematic diagram of a first embodiment of the invention.

Figure 2:
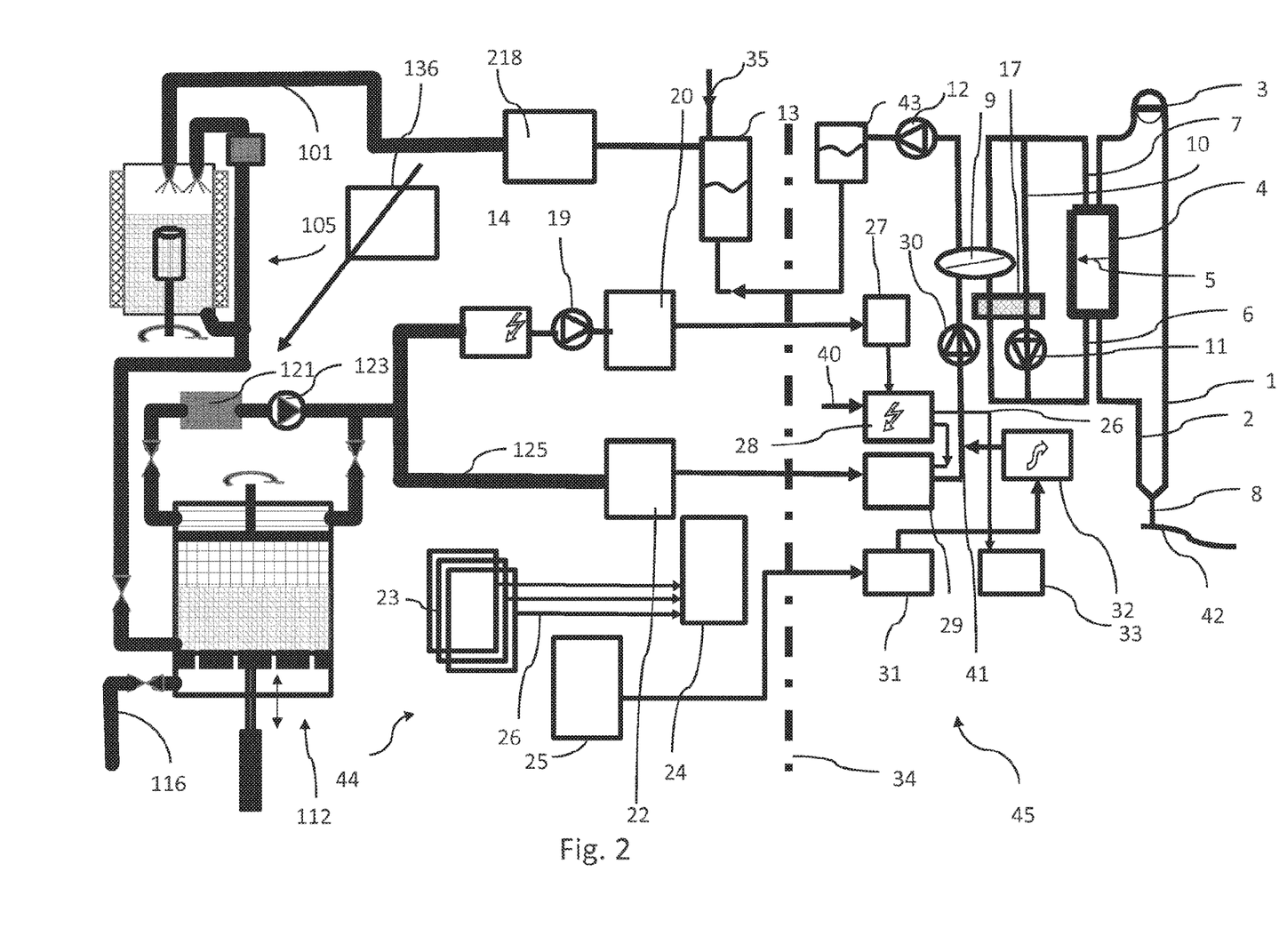
FIG. 2 is a schematic diagram of a dialysate apparatus according to an embodiment of the invention.

FIG. 2 is a schematic diagram of a dialysate apparatus according to an embodiment of the invention.

FIG. 1 shows an embodiment of the invention wherein the dialyzer is to be connected to the dialysate inlet 101 and the pure water outlet (or dialysate outlet) 125.

FIG. 1 is a schematic diagram of the cryopurifier 130 of the embodiment of the invention. The cryopurifier 130 comprises a crystallizer, i.e. a container for ice crystal growth 105. There is a cooling jacket 106 for cooling the content of container 105. The dialysate inlet 101 provides dialysate from the dialyzer 4 (see FIG. 2) which is sprayed into container via dialysate inlet nozzle 102.

The ice slurry 107 inside container 105 is stirred by stirrer 108 and discharged to feedback line 109 for optional seed preparation and slurry feed line 110 to the wash column 112. Feedback line 109 feeds a portion of the ice slurry 107 to crystallizer-heater-cooler unit 103 and then to seed crystal inlet nozzle 104.

There are several valves 114 for flow control which are regulated according to the knowledge of the skilled person.

The ice slurry 107 from container 105 is feed into wash column 112 via slurry inlet 111.

A hydraulic piston 113 can be used to push slurry through the wash column 112, i.e. through liquid phase filter 115. At the bottom of wash column 112 there is outlet 116 for discharging concentrate. At the left side of the top of wash column there is a pure slurry pipe 122 through which solid and liquid is pumped in the direction of pure water outlet 125. A portion of the pure water is fed into pure water feedback loop 124 which is connected to the right hand side of the top of the washing column.

Due to the pressure of pump 123 pure water is fed into wash column 112 and rinsing through the ice slurry in the wash column across wash front 118. Thereby concentrate is washed from the ice and concentrated at the bottom of wash column 112 such it can be discharged through concentrate outlet 116. Due to the wash front 118 there is essentially pure ice and pure liquid 119 at the top of wash column 112. At the top there is a rotating ice scraper 120 which scraped off the top layer of the wash front such that on top thereof pure slurry 126 is obtained which is fed into pure slurry line 122 via the suction of pump 123. A heater 121 can be used to generate pure water from the pure slurry.

Optional means 218 for pre-purifying the dialysate can be provided. For instance a distiller and/or a reverse osmosis system and/or a fat separator can be provided in the dialysate feed line before the dialysate inlet 101 as shown in FIG. 2.

Optional there is provided a heat exchanger 136 between the dialysate inlet 101 and heater 121 as shown in FIG. 2.

FIG. 2 shows an embodiment according to the invention. A catheter 8 is inserted into a vein 42 of a patient. The catheter is y-shaped wherein one leg of the Y-catheter 8 is connected to the blood inlet 1 and the other leg of the y-catheter 8 blood outlet 2. The catheter 8 can be a single-needled (SN) or a double needled (DN) catheter. A blood pump 3 is provided to pump the blood of the patient from vein 42 to the dialyzer 4. In the dialyzer 4 an ultrafiltrate transfer 5 takes place. There is a dialysate circuit flowing in opposite direction through the dialyzer 4 having a dialysate inlet 6 and a dialysate outlet 7. In the dialysate circuit there is a priming shunt 10 and a priming pump 11 provided. This allows to fill the machine completely with ultrafiltrate from the patient initially when dialysis is started first time. Furthermore there is a volume balancing unit 9 coupling the dialysate circuit with a fresh water circuit. The specific design of the dialyzer and balancing system and the above mentioned components are known to the skilled person.

An ultrafiltrate dosage pump 12 is pumping the dialysate to the spent dialysate reservoir 13. Optionally water from other sources can also feed into the spent dialysate reservoir 13 via optional line 35. However it is preferred to use the dialysate obtained from the dialyzer only.

The dialysate is then fed into a cryopurifier. The cryopurifier can comprise an ice crystal growth container 105 and a wash column 112. The details thereof are shown in FIG. 1. The same reference numerals have been used in FIG. 2 and reference is made to the description of the FIG. 1 embodiment.

There are several heating means 17 used to keep the materials at an appropriate temperature level. Heating means are known to the skilled person and do not need to be described in more detail here.

The optimum working temperature of the cryopurifier is below 0° C. and above the eutectic temperature.

The pure water obtained by the cryopurifier is fed into pure water reservoir 22. There is a dosage/admixture unit 32 providing appropriate amounts from a storage means 25 and 31 to the pure water via dosage line 41, such as NaCl, Bic and anticoagulation, such that fresh and individual dialysate is obtained for further usage. Pump 30 is driving this fresh dialysate to volume balancing unit 9.

Energy is provided by photovoltaic solar panels 23. Other power supply means can be used in addition and/or alternatively. Electrical power supply lines are provided for supplying electrical power to the various components. Some of them are shown in the figures. In addition there is a power and control unit 24 for driving the apparatus shown in the figures.

The apparatus shown in FIG. 2 is separated into a base station 44 at the left hand side and a wearable unit 45 at the right hand side. The wearable unit is designed such that the patient can keep the wearable unit at the person in order to have the option of continuous dialysis similar to the function of kidneys. The wearable unit can be recharged in intervals at the base station. It will be possible to have one or more portable portions for one base station, depending on the size and capacity of the base station. It will also be possible to recharge and service the portable portion at different base stations. However it is preferred to have one base station for one patient because then the cleaning requirements do not need to be as high as for installations where different patients are using the same base station.

The device shown in FIG. 2 has a docking interface 34. As shown in FIG. 2 some reservoirs of FIG. 1 are separated into a large reservoir for the base station and a smaller reservoir for the wearable unit.

Accordingly the wearable unit 45 comprises a small dialysate reservoir 13 to be connected with the dialysate reservoir 13 of the base station 44, a small hydrogen reservoir 27 to be connected with the dialysate reservoir 20 of the base station 44, a small water reservoir 29 to be connected with the water reservoir 22 of the base station 44, and a small store means 31 to be connected with the store means 25 of the base station 44. The docking interface is designed such that the materials can be discharged (44 to 13) and recharged (20 to 27, 26 to 29 and 25 to 31) in a few minutes or even less—in particular comparable to a lavatory visit. Optionally energy can be charged into the wearable unit if needed.

In addition the wearable unit 45 may comprise a local hydrogen fuel cell 28 to be used as power supply for the wearable unit 45. To save weight, the local hydrogen fuel cell 28 uses oxygen 39 from the environmental air. Optional additional or alternative power supplies known to the skilled person can be provided.

The wearable unit 45 may comprise a local power and control unit 33.

The setup of FIG. 1 can be used for cryopurification of dialysate. It comprises a crystal growth system and a washer column. Both elements depict a symbolic embodiment and must be understood as a possible realisation of generating ice crystals as a means of water purification in dialysis.

According to an embodiment of the invention the components of the wearable unit 45 and the base unit 44 can be combined in a wearable unit only. Alternatively they can also be combined in the base unit only.

In another technical context than dialysis not the purification but the gentle concentration without heat degradation is of interest. Fruit juice concentration would be an example where not the pure water (25 in FIG. 1) but the concentrate (16 in FIG. 1.) is further processed. To the knowledge of the inventor however this principle has never been applied to a dialysate preparation system of a wearable artificial kidney (WAK) as depicted in FIG. 2. The adoption of this principle to a base station of an independent dialysis system that therefore permits access to ultra pure water fed alone from the patients ultrafiltrate or spent dialysate is an unexpected combination of two well established technologies that in their combination allow for hospital independent dialysis. This has never been considered In particular the separation in a base station and a wearable part in combination with the cryopurification of dialysate makes the system very versatile. This is shown in the embodiment of FIG. 2.

The embodiment of FIG. 2 shows the invention with respect to a dialyzer. It is also possible to use the aspects in the context of peritoneal dialysis as mentioned before.

FIG. 2 shows the integration of a cryopurification system into a dialysis system consisting of a base station and a wearable artificial kidney {WAK). Using solar power its operation can be autonomous without supply from mains or external feed of water other than from the patient's ultrafiltrate. The system is lightweight and has low power requirements so that it can be operated even in a car. As the base station has no costly components a single patient may also operate several base stations each located at different whereabouts so that an extended independence unknown before to dialysis patients can be realized. The operation time of the wearable part is in the range of 3 h before another 45 s recharge has to be conducted. The facultative fueling using hydrogen and fuel cells is superior to accumulators when it comes to low weight energy packing and quick rechargeability.

According to the considerations of the principle's secure and intrinsic ice purity mentioned above the energy requirements for purification are moderate compared to distillation (334 kJ/kg compared to 2257 kJ/kg)—which is roughly ⅐. This makes 18 h per day low flux dialysis with approximately 25 ml/min dialysate flow very cost effective as per hour of dialysis an amount of 1.5 l or 83.3 moles of water would be needed. The electrical power needed to perform the process is 140 W without heat reclamation. This is sufficiently low to be driven even by a car generator or solar panels. Alternatively or in addition energy supply can be made with propane gas bottles. Propane has the advantage that is can be burnt directly in the fuel cells.

This allows for decentral operation of the base station far off electrical power supply or pure water resources. In particular the latter is fulfilling an urgent need of millions of dialysis patients in the developing world. The system can be built sufficiently small to be positioned in a sideboard or in a car.

The separation by a base station and a wearable part reduces the patients burden to a restriction that is not beyond the restriction the frequent regular attendance to a lavatory imposes to healthy people. The key is to transfer all substances and energy via the dedicated connection interface within 30-45 s. For a 3 h treatment 4.5 l of pure water have to be flushed into the wearable part as well as the same amount of the previous period has to be discarded from it. Further the electrolytes, anticoagulants, glucose and other ingredients of freshly prepared dialysate have to be transferred. An issue could be the energy transfer to the heating and pumps of the dialysate. As long as accumulators are used, they have to be replaced using a click system known from cordless drills or the like. As the electrical power required for heating, several pumps and control in the wearable part is in the range of not less than SOW, a safe 3 h operation would need a 12V 12 Ah accumulator. The size and weight of such an accumulator might be reduced further in the future but is still an additional weight burden of 2-3 kg depending on the state of the accumulator art in use. Recharging and aging of these accumulators would be another issue. Although it is possible to fuel the wearable part by accumulator it is advantageous to fuel it by a small fuel cell and hydrogen tank for weight and instant recharge reasons. This technology utilizes the high energy per weight of hydrogen. An amount of 270 ml compressed hydrogen at 20 MPa {200 bar} has a weight of only 5g, can be flushed in 30 s and further can fuel the wearable device for 3 h. Even quadrocopters use this technology nowadays in preference to accumulators.

The technology combination of cryopurification, hydrogen fueling and separation of dialysis machines into one or more base stations at different locations and a quickly rechargeable wearable part of only a few kilograms of weight that can be worn in a vest reveals an unexpected advantage to the expert of the field—as well as to the patients and has high potential for cost reduction and enhancement of the patients ability to participate in social life and work. Further the principle allows for 18 h dialysis per day or even for overnight dialysis. From a technical aspect the dialysis must be interrupted only for maintenance, which should not be more than 30 min per day at a time chosen by the patient. This will significantly reduce mortality and improve personal health and long term outcome of the patients.

There are different technical embodiments for the system. The control of ice cristallization can be performed using infrared spectroscopy at wavenumbers around 3200 cm−1. The wash column can be operated using pistons, unsing threaded bolts rotating, using gravity or electrical drive. The crystallizer can be integrated or be omitted as it influences mainly crystal size and therefore controls surface/volume ratio of the ice crystals. Crystal seed ratio and supercooling can be adapted or not be adapted. This affects crystal size and purity after washing but is not essential to the principle itself.

The injection of the dialysate can be performed using nozzles or just simple inlets, as well as the geometric configuration of the cooling surface can be modified.

The dwell time or type of operation (batch or continuous) of the dialysate in the crystal grower can be varied according to the throughput required. This influences the process of Ostwald ripening [22] but does not prohibit utilization of the principle itself. Even external heat exchangers (236 in FIG. 2) can be applied or not applied. The degree of supercooling is varied or not varied and will influence ice ripening times and purity after washing.

Additional crystal growth activators like glucose can be used or not be used as they are washed out in the wash column.

In the method according to the present invention, a dialysate is reclaimed. A dialysate is an aqueous solution used in the hemodialysis to remove substances from the blood. The dialysate can contain electrolytes, glucose and buffer substances in a composition similar to the blood serum. Substances obligatory excreted by the kidneys contained only in the blood diffuse into the dialysate or are extracted by convection. Substances obligatory excreted by the kidneys are molecular end products (catabolites) of the metabolism, which have to be excreted continuously with the urine. Hereinafter these substances are also referred to as uremic toxins or solutes in connection with step (a) of the method of the present invention. As a result of the method, the fresh dialysate is obtained that can be reused for dialysis. The cryopurification unit can also be used to generate online fluid substitute for hemodiafiltration or peritoneal dialysis.

In step (a) of the method, an ice slurry is formed from the dialysate, wherein the ice slurry contains pure ice crystals and a liquid containing remaining solutes, wherein the solutes comprise the above mentioned substances obligatory excreted by the kidneys. The ice slurry can be prepared by freezing the dialysate. As it is described in the following in detail, the ice crystals contained in the ice slurry are of high purity and the undesirable substances (solutes) mentioned above are maintained in the liquid.

By the separation in step (b), in which the ice crystals are removed from the liquid containing the solutes, as a result it is possible to separate the ice crystals from the solutes. When the ice crystals are thawed, water of a high purity is obtained which allows it being used again for the dialysate.

The method is suitable for reclaiming fresh dialysate from an ultrafiltrate and wasted dialysate extracted from the hemodialysis or peritoneal dialysis patient in particular without further external water admixture or treatment-/patient-related disposables for water reclamation like cartridge, filters or semipermeable membranes except the dialysis filter itself. It is possible to use the reclaimed fresh dialysate for the same patient from which the ultrafiltrate or the washed dialysate is obtained. In the method, at least about 80% of the month average primary ultrafiltrate or wasted dialysate volume amount can be extracted from one or several patients subjected to reclamation and afterwards can be fed back to the dialyzer or peritoneum of the same patient and not more than about 20% of it being discarded.

The temperature of step (a) can be between 0° C. and the eutectic temperature.

In step (a) of the method a crystal seed can be used, like ice crystals. When crystal seeds are used in step (a) it is possible to obtain more homogenous single ice crystals in a homogenous size distribution. The single crystals do usually not exceed 500 µm. Furthermore, the ice crystals are obtained with high purity as they contain less internal lattice fractures that might enclose impurities.

In step (a) of the method it is possible to use crystal growth activators. Such crystal growth activators function as starting point for the crystallization. By using crystal growth activators, it is supported to obtain more homogenous single crystals in a homogenous size distribution. The single crystals do usually not exceed 500 µm. Furthermore, the ice crystals are obtained with high purity. For example, the crystal growth activator is glucose, with which the above effects are achieved in a particular advantageous way and, furthermore, it is a physiological occurring substance.

Step (a) of the method can be carried out by supercooling. Supercooling, also known as undercooling, is the process of lowering the temperature of a liquid or a gas below its freezing point without it becoming a solid. In particular, it is referred to the so called constitutional supercooling. Here it plays a role how fast a given delta V is cooled, because the local change of the melting point near the eutectic (liquidus line) is greater as the change of the temperature over this area. Therefore, it is possible to influence whether the eutectic can leave the boundary of the formation of the liquid-ice phase boundary fast enough or whether from a energetically point of view a crystal fracture is formed. Supercooling is lowering the temperature point, at which the crystallization starts, but accelerates the process (as dx/dt of the phase boundary). Therefore, it is a good parameter to control insertions into the crystal and the mature time. The presence of a eutectic itself is, however, an energetic barrier for the process of supercooling, because it might work as a crystallization seed and thus remove too early the energetic situation, in which supercooling can occur.

The control of ice crystallization can be performed using infrared spectroscopy at wavenumbers of 3200 cm−1. In particular, the start of the crystallization can be monitored so that the crystallization can be controlled and regulated so that as a result it is possible to obtain ice crystals having a good homogeneity and a suitable size distribution.

In step (b) of the method, the ice crystals can be separated from the liquid. It is possible to carry out this step by any method of separating solids from liquids known to the skilled person. For instance cryopurifying may be used for separating solids from the water. Also freeze concentration may be used for separating solids from the water. Freeze concentration is normally used for removal of pure water in the form of ice crystals at sub-zero temperatures. It is used for getting juice concentrates wherein the concentrated product is to be obtained. According to the invention it is the opposite, i.e. the pure water is to be obtained and reused as dialysate for the patient. For freeze concentration a crystallizer, a vessel with a cooling jacket and a wash column is used.

According to the method, a wash column or an equivalent method to separate water ice crystals from a liquid phase with simultaneously rinsing their surface from impurities is employed.

It is not suitable to filter the ice slurry since ice h has the property to melt at pressing points and thus to change the form. Due to the inhomogeneous form of the crystals there would occur such a pressing point in a filter pore at which the crystal melts. Therefore, it would penetrate through the filter pores by an adaptive change of the form and the effect of filtering would disappear.

Therefore, a wash column or equivalent methods to separate ice crystals from a liquid phase with simultaneously rinsing their surface from the impurities is used.

The use of a washing column is shown in FIG. 1. A mixture of a solid pure phase and a liquid phase with impurities is pressed, for example from the below, into the cylinder of a washing column. For this pressing a certain force can be applied. At the other end, for example at the top of the column, there is an ice scraper, for example a knife or a blade, which separates a thin pure layer. This scraped pure ice is thawed. A small part of the thus purified water is pressed back into the washing column from the above.

Pure water is freezed at 0° C., but impure water freezes below down to the eutectic temperature with a maximal contamination. Therefore, the melting temperature depends from the degree of contamination in the sense the more contaminated the lower the melting point. The ice of the topmost layer, where it is scraped, has a temperature of exactly 0° C. (pure water and ice can coexist at 0° C.). Thus, the pure ice of the topmost layer is bathed in pure water. Should there be adhering impurities at the surface of the ice, they are delivered to the back flowing water thawed from pure ice, and thus the melting point is lowered. Therefore, it remains liquid. Since to the bottom the temperatures decrease, the water is going to penetrate into the cracks of the ice crystals and rinsing them until the surrounding ice coming from below reaches the melting temperature of the rinsing water. At this moment it freezes again to pure ice and releases the impurities. The pure ice is then pushed towards the scraper, where there is always pure ice, from which pure rinsing water can be prepared. Again at the freezing of the back flowing rinsing water the impurities remain in the liquid phase and rinse the surface. By these steps the liquid phase is concentrated more and more. At the point at which it remains liquid at a given impurity degree of the raw water there is formed the washing front. Below this region the concentration of the liquid phase is so high that it does not freeze any more at the temperature of the succeeding ice (which is above the eutectic temperature). Consequently, it can be removed as liquid phase downward.

Of course, the invention is not limited to the embodiments shown in the drawings. Therefore, the above description should not be considered limiting but explanatory. In so far as the above description defines "first" and "second" features, this designation serves for distinguishing two similar features without determining an order.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. An apparatus for generating dialysate for dialysis comprising:
   a dialysate outlet;
   a dialysate inlet; and
   a cryopurifier for generating pure water, wherein an inlet of the cryopurifier is connected to the dialysate outlet and an outlet of the cryopurifier is connected to the dialysate inlet.

2. The apparatus according to claim 1, wherein the cryopurifier comprises an ice crystal growth container and a wash column.

3. The apparatus according to claim 1, wherein the outlet of the cryopurifier comprises a pure water outlet connected to the dialysate inlet.

4. The apparatus according to claim 1, further comprising a dialysate prepurifier provided between the dialysate outlet and the cryopurifier inlet.

5. The apparatus according to claim 1, further comprising a dialysate postpurifier provided between the cryopurifier outlet and the dialysate inlet.

6. The apparatus according to claim 1, further comprising a heat exchanger for providing heat exchange between the cryopurifier inlet and a heater at the cryopurifier outlet.

7. The apparatus according to claim 1, further comprising a base station and a wearable unit.

8. The apparatus according to claim 7, wherein the cryopurifier is integrated in the wearable unit.

9. The apparatus according to claim 7, further comprising a docking interface for connecting the base station with the wearable unit.

10. The apparatus according to claim 1, wherein the dialysate inlet comprises an inlet of a dialyzer and the dialysate outlet comprises an outlet of the dialyzer.

11. The apparatus according to claim 1, wherein the dialysate inlet comprises a peritoneal dialysis inlet and the dialysate outlet comprises a peritoneal dialysis outlet.

12. A method for reclaiming fresh dialysate from ultrafiltrate and a wasted dialysate extracted from a dialysis patient, the method comprising:
   preparing an ice slurry from the wasted dialysate, wherein the ice slurry contains a plurality of ice crystals and a liquid containing solutes; and
   separating the ice crystals from the liquid containing the solutes.

13. The method according to claim 12, wherein the preparing the ice slurry from the wasted dialysate is carried out at a temperature between 0° C. and a eutectic temperature, wherein the eutectic temperature is lower than 0° C.

14. The method according to claim 12, wherein the preparing the ice slurry from the wasted dialysate further comprises using a crystal seed and applying a crystal growth activator, wherein the crystal growth activator is glucose.

15. The method according to claim 12, wherein the preparing the ice slurry from the wasted dialysate further comprises in supercooling.

16. The method according to claim 12, wherein the preparing the ice slurry from the wasted dialysate further comprises controlling ice crystallization by infrared spectroscopy, Raman spectroscopy, or a combination thereof.

17. The method according to claim 12, wherein the separating the ice crystals from the liquid further comprises cryopurifying.

18. The method according to claim 12, wherein the wasted dialysate is recirculated.

19. The method according to claim 12, wherein the liquid containing the solutes is analyzed like urine.

20. The method according to claim 12, wherein the separating the ice crystals from the liquid further comprises freeze concentrating.

* * * * *